United States Patent [19]

Moukheibir

[11] Patent Number: 4,490,137
[45] Date of Patent: Dec. 25, 1984

[54] SURGICALLY IMPLANTABLE PERITONEAL DIALYSIS APPARATUS

[76] Inventor: Nabil W. Moukheibir, 2636 Suffolk St., Kingsport, Tenn. 37660

[21] Appl. No.: 428,831

[22] Filed: Sep. 30, 1982

[51] Int. Cl.³ .............................................. A61M 5/00
[52] U.S. Cl. ...................................... 604/28; 604/29; 604/175; 604/116
[58] Field of Search ................................ 604/27–29, 604/175, 116

[56] References Cited

U.S. PATENT DOCUMENTS

| | | | |
|---|---|---|---|
| 3,402,710 | 9/1968 | Paleschuck | 604/175 X |
| 4,160,454 | 7/1979 | Foux | 604/175 X |
| 4,184,497 | 1/1980 | Kolff et al. | 604/29 X |
| 4,256,102 | 3/1981 | Monaco | 604/29 X |
| 4,362,157 | 12/1982 | Keeth | 604/116 |
| 4,405,305 | 9/1983 | Stephen et al. | 604/29 X |
| 4,417,888 | 11/1983 | Cosentino et al. | 604/29 X |

FOREIGN PATENT DOCUMENTS 2390940 1/1979 France ................................ 604/29

Primary Examiner—Dalton L. Truluck
Attorney, Agent, or Firm—Malcolm G. Dunn

[57] ABSTRACT

A surgically implantable apparatus for subcutaneous placement in the body of a patient and by which peritoneal dialysis may be performed with minimal risk of infection, the apparatus being connected to a catheter extending into the peritoneal cavity and having a needle-impenetrable reservoir, a needle-penetrable covering over the opening of the reservoir, and an essentially nonyielding support extending across reservoir opening beneath and contiguous to the needle-penetrable covering to prevent sagging of body tissues; and a method for performing peritoneal dialysis by means of the apparatus.

9 Claims, 6 Drawing Figures

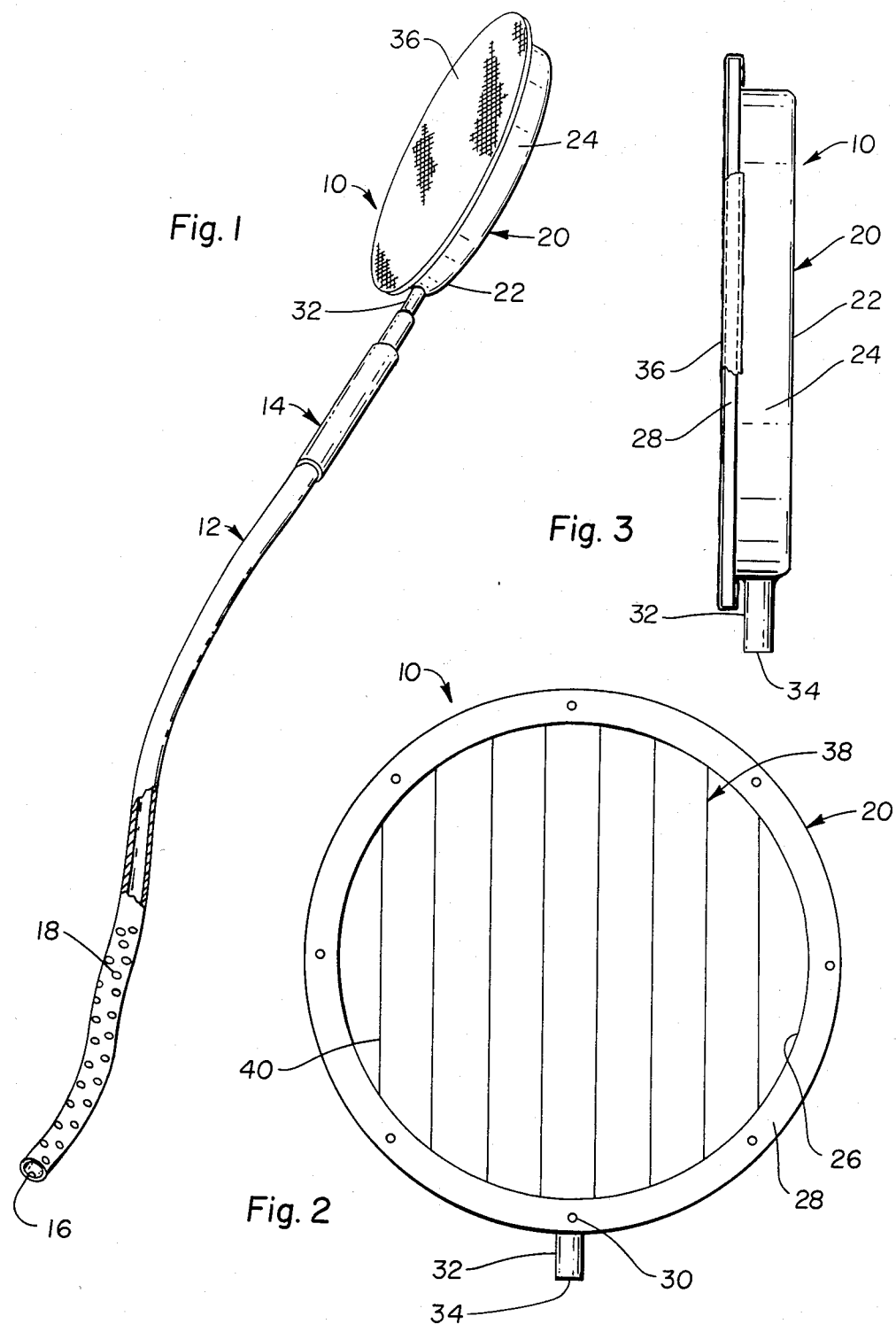

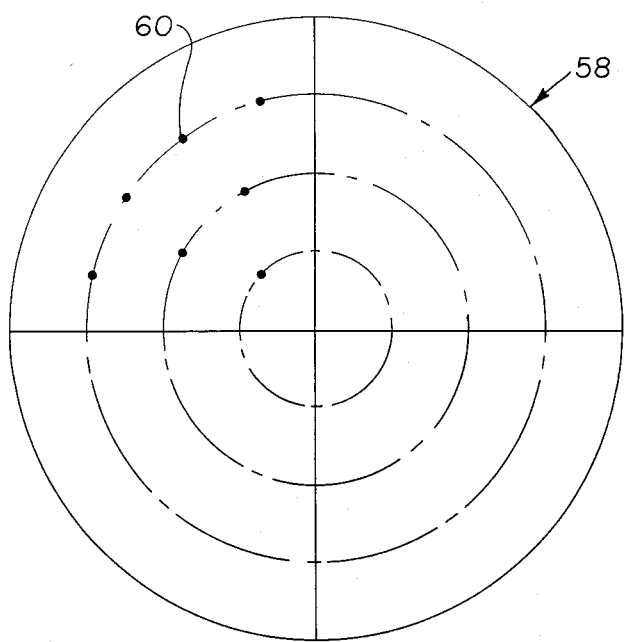
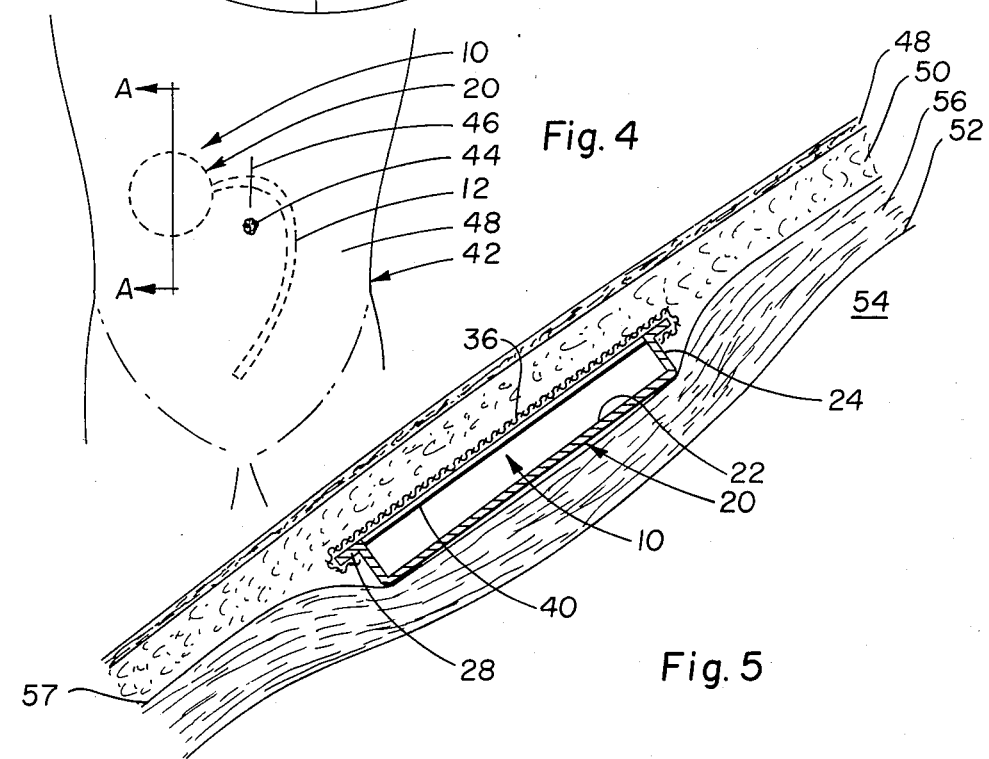

SURGICALLY IMPLANTABLE PERITONEAL DIALYSIS APPARATUS

DESCRIPTION

1. Technical Field

The present invention relates to an apparatus adapted to be surgically implanted in the body of a patient and by which peritoneal dialysis may be performed with negligible risk of peritonitis, and to a method for performing peritoneal dialysis by means of the apparatus.

2. Background Art

The invention relates to a dialyzing system involving the introduction of dialyzing fluids, the dialysate solution, into the peritoneal cavity of the patient, which is lined by the peritoneal membrane, the membrane being highly vascularized. A tube called a "catheter", such as a Tenckhoff peritoneal dialysis catheter having an opening at one end and a series of perforations extending through the tube wall along a predetermined length of the tube from that one end, is surgically implanted and secured within the peritoneal cavity and the other end projects through the skin of the patient. The dialyzing fluid or dialysate solution is introduced into the patient's body by opening the external end of the tube that projects from the patient's body and passing the dialyzing fluid through the tube and out of the perforations and end opening into the peritoneal cavity where the fluid remains for a predetermined time period and in a quantity and quality sufficient to allow the toxins from the blood to cross the peritoneal membrane to the dialyzing fluid. The dialyzing fluid is later removed along with the toxins by syphon or a gravity technique through the same tube.

The external end of the tube projecting from the patient, however, has not been satisfactory for several reasons, the primary one being the risk of serious infection, peritonitis, when this type of dialysis is being performed. Even if the patient or the health personnel are especially careful to keep the tube closed at all times when the tube is not in use, bacteria may enter the tube when connecting the tube to the source of dialyzing fluid. The patient also has to be especially careful when taking showers or swimming. In order to avoid these problems and others not mentioned, there have been proposals that the tube or catheter be connected to an apparatus or device that is surgically implanted, after which injections are then made through the skin of the patient and into the apparatus or device.

For instance, in U.S. Pat. No. 4,160,454, there is disclosed an elongated hollow member or casing which is adapted to be implanted in the subcutaneous fat layer of a person. The "fat layer" is located between the skin and the fascia of the person. A tube extends generally laterally from one end of the elongated hollow member or casing, one end of the tube passing through an opening in the hollow member or casing and the other end extends through the fat layer, fascia, muscle tissue and peritoneal membrane into the peritoneal cavity. The hollow member or casing is made from a material such as silastic rubber, which is penetrable by a hypodermic needle. The casing is reinforced by a coil of wire, which prevents the casing from collapsing when the needle is inserted or when liquid is withdrawn from the casing. The tube itself is made of flexible silicone rubber and has a plurality of openings near the free end of the tube to allow the flow of liquid through the openings into or out of the tube. After the hollow member or casing and its tube have been surgically implanted, a hypodermic needle is inserted through the skin into the casing and the dialysis solution is introduced through the hypodermic needle into the hollow of the casing. The liquid flows from the casing into the connected tube and out of the openings at the free end of the tube into the peritoneal cavity. The needle may then be withdrawn leaving only a readily healable wound in the patient's skin. The hole in the casing wall is said to be "rapidly sealed by tissue growth", to thus prevent any outflow of liquid through the hole. The exterior surface of the casing is treated to enhance and accelerate the growth of human tissue, such as by covering the casing with a polyester resin velour or a porous polytetrafluoroethylene.

There appear, however, to be some significant disadvantages to the structure disclosed in U.S. Pat. No. 4,160,454. For one, the target area under the patient's skin to be contacted by the hypodermic needle is rather narrow and there is the risk of missing the casing altogether when injecting the hypodermic needle. A greater risk exists, however, due to the nature of the material used to construct the elongated hollow member or casing as well as the narrowness of the target area. There is the risk that due to the rubbery character of the casing the needle could pass through one side and out the other side of the casing or undesirably directly into the peritoneal cavity without the patient or the health personnel being aware of it until he or she attempted to introduce the dialysate solution, and of course he or she will not be aware of it if it goes directly into the peritoneal cavity.

U.S. Pat. No. 4,184,497 discloses an implantable catheter having at one end thereof an enlarged, hollow, needle-pierceable member, which is implanted to extend horizontally under the skin of the abdomen of the patient when erect. The enlarged hollow member defines two bends with the first bend directing the catheter inwardly from the horizontally positioned hollow member, and with the second bend directing the catheter downwardly toward the "pelvic gutter" or bottom of the peritoneal cavity. The horizontal positioning of the hollow member is for the purpose of giving greater needle puncturing area across the width of the patient. The enlarged hollow member is made of a material such as silicone rubber, and a precoiled stainless steel spring embedded within the material gives the hollow member sufficient rigidity to withstand collapse upon repeated puncture by needles, as well as to provide a bulge in the skin for easy location of the hollow member for penetration by a needle. The hollow member is covered with a polyester velour to encourage tissue adhesion after implantation has taken place. One disadvantage would appear to be the risk that the patient might extend the needle through the rubbery material of the hollow member too far causing it to pass through one side of the hollow member and out the other side or directly into the peritoneal cavity. Another disadvantage would appear to be the discomfort suffered by the patient because of the bulge and rigidity of the hollow member as it extends across a significant portion of the width of the patient.

U.S. Pat. No. 4,256,102 discloses the free end of the implanted catheter as being open and preferably flared like a funnel, with the funnel section adapted to be implanted subcutaneously preferably at the level of the fascia. The funnel is said to be preferably molded of a suitable inert, durable, resilient and soft surgical grade plastic such as silicone. The open end of the funnel section is covered with a needle perforable nylon mesh, which is designed to allow the tip of a needle to be forced between the interstices of the mesh without damaging it while at the same time providing a means for preventing fat or other tissue from moving into the interior of the funnel section. The mesh is tight enough to hold the dialyzing fluid in the catheter after fibrous ingrowth has sealed the mesh. When it is necessary to dialyze the patient, the wide end of the funnel section is manually located, the area over it is antiseptically prepared and a needle is then pushed through the skin of the patient until its pointed end enters the funnel section. The arrangement described would appear to have a number of disadvantages. For one, due to the slope of the funnel section and the rubbery nature of the material with which the funnel section is made, the patient runs the risk of extending the needle too far, thus passing out the other side of the funnel section and possibly into the peritoneal cavity. More significantly, however, is that the nylon mesh is stretched across the opening of the funnel section and is otherwise unsupported. In time the tissue ingrowth would tend to intrude further into the funnel section causing sag when attempt is made to inject the needle and thus leaving little or no scope for the needle to enter the interior of the funnel section before it would undesirably penetrate through the wall of the funnel section. This is not true of the present invention which has an essentially nonyielding support arrangement beneath and contiguous with the undersurface of the mesh that extends over the opening of the disclosed surgically implantable apparatus.

U.S. Pat. No. 3,752,162 discloses an implantable device for providing a long term percutaneous pathway for elongated members such as catheters, pacemaker leads, fiber optics, and the like, comprising a flanged cup-shaped body containing coils of the elongated member or members. A membranous member such as silicone rubber may extend across the opening of the device, and the device has at its bottom at least one aperture through which the elongated member or members pass and to which the elongated member(s) may be permanently affixed. After the device has been surgically implanted and the patient has healed, an incision is made through the skin overlying the device and also through the membranous covering so that the coiled end of the elongated member(s) can be withdrawn through the incision and then connected to the necessary "extracorporeal" equipment to be associated with the device. This device is otherwise different from the apparatus or devices shown in the other patents described above and from the apparatus of the present invention in that no injection is made by a needle through the skin of the patient and into the device due to the fact that the elongated member is designed to extend outside the patient's body and through which fluids could be introduced into the body of the patient.

DISCLOSURE OF THE INVENTION

In accordance with the present invention, I provide a surgically implantable apparatus that is adapted for subcutaneous placement in the body of a patient and by which peritoneal dialysis may be performed. The apparatus has a reservoir which defines a first wall, and a peripheral wall formed at the periphery of the first wall at about right angles thereto and extending a predetermined distance therefrom and defining at its free end an opening opposite the first wall. The reservoir is formed from a needle-impenetrable material. A needle-penetrable covering extends across the opening of the reservoir and is suitably secured to the peripheral wall and is sufficiently permeable to allow body tissue ingrowth to occur and to seal the surface of the covering when the apparatus is implanted in a patient. An essentially nonyielding support is provided for the needle-penetrable covering and extends across the opening of the reservoir beneath and contiguous with the undersurface of the covering. This support is suitably fixed to the peripheral wall and is spaced at predetermined intervals across the undersurface of the covering. A nozzle extends from the reservoir and has an opening extending therethrough and into the interior of the reservoir. The nozzle is adapted to receive thereover one end of a catheter that will extend into the peritoneal cavity of the patient.

The peripheral wall may have a flange formed at its free end around its periphery and extending outwardly from the peripheral wall at about right angles thereto. The flange defines through its surface at predetermined intervals a series of holes of a size suitable to receive therethrough a suturing thread.

The reservoir is preferably formed from a metal such as titanium, a relatively inert material with respect to the body tissues.

The covering is preferably suitably secured to the flange of the reservoir.

The nozzle preferably extends from the peripheral wall.

The essentially nonyielding support may comprise a series of spaced parallel bars.

The essentially nonyielding support may comprise a series of spaced bars that are formed in a predetermined pattern.

Also, in accordance with this invention, I provide a method of performing peritoneal dialysis on a patient in whose body the apparatus described above has been suitably surgically implanted in such manner that the opening in the reservoir and the needle-penetrable covering of the apparatus are spaced below and parallel to the skin of the patient and a catheter has been connected to the nozzle of the apparatus and extended in the peritoneal cavity of the patient. My method comprises providing on the surface of the skin of the patient, which is at a location overlying the opening in the surgically implanted apparatus, a diagram corresponding approximately in size and configuration to the opening. The diagram is divided into approximately equal segments in size and configuration and has a series of marked points within each segment at predetermined intervals. Each marked point designates the site for the entry of a needle-injection, and the spaced intervals correspond to the spacing necessary to avoid a yet unhealed area caused by more recent needle-injections. Each needle injection is then made at a marked point different from the previous needle-injection and follows a predetermined path from one marked point to the next marked point within each of the segments.

The diagram in my method may be in the configuration of a circle and the series of marked points may be located at spaced intervals along concentric circular paths relative to the center of the opening and the circle may be divided into quarter segments.

BRIEF DESCRIPTION OF THE DRAWINGS

The details of my invention will be described in connection with the accompanying drawings, in which FIG. 1 is an isometric view of the apparatus by which peritoneal dialysis may be performed when surgically implanted in a patient;

FIG. 2 is a plan view of the reservoir of the apparatus and illustrating the spaced parallel bars of the support for the covering, the flange, the openings in the flange and the nozzle to which a catheter may be attached;

FIG. 3 is an elevational view of the reservoir of the apparatus and illustrating the flange and the covering extending across the opening of the reservoir and secured to the flange;

FIG. 4 is a diagrammatic view of a human body illustrating one possible location of the surgically implanted apparatus and catheter;

FIG. 5 is a cross-sectional view taken along line A—A of FIG. 4 of the abdominal wall of a patient illustrating the surgically implanted apparatus of the invention, and showing the location of the surgically implanted apparatus relative to the skin, subcutaneous fat, fascia, muscle layer, peritoneum, and peritoneal cavity of the patient; and FIG. 6 illustrates a diagram which may be provided on the skin surface of the patient at a location overlying the opening of the surgically implanted apparatus of this invention in accordance with the method of my invention.

BEST MODE FOR CARRYING OUT THE INVENTION

In reference to the drawings and initially to FIG. 1, 10 designates the surgically implantable apparatus of my invention which is adapted for subcutaneous placement in the body of a patient and by which peritoneal dialysis may be performed. The apparatus 10 has a tube or catheter 12 attached to it, the catheter being adapted to extend from the apparatus and into the peritoneal cavity of the patient and through which the dialysate solution may be introduced into the peritoneal cavity and later removed therefrom along with accumulated toxins and the like. A cuff 14, such as a velour covering of polyester material, is provided around the tube or catheter at the location shown in FIG. 1 and serves a purpose which will be described later. The free end of the tube or catheter 12 has an opening 16, and a series of perforations 18 extend through the wall of the tube along a predetermined length of the tube. When the dialysate solution is introduced into the apparatus by hypodermic injection in a manner that will be described, the dialysate solution flows from the apparatus into the tube or catheter and out through the perforations 18 and opening 16 into the peritoneal cavity of the patient. Later, the dialysate solution and accumulated toxins and the like return through the opening and perforations when a vacuum technique is applied or drainage is effected by gravity.

The surgically implantable apparatus 10 per se comprises a reservoir 20 which is formed from a needle-impenetrable material, preferably an inert metal with respect to the body tissues such as titanium. The reservoir is preferably disc-like in configuration so as to minimize as much as possible any discomfort to the patient. The reservoir defines a first wall 22, preferably circular, and a peripheral wall 24 that is formed at the periphery of the first wall 22 at about right angles thereto and extends a predetermined distance therefrom, such as about 10 millimeters. With a circular reservoir the first wall 22 will also be circular and the peripheral wall will extend circumferentially around the periphery of the first wall. The peripheral wall defines at its free end an opening 26 (see FIG. 2) opposite the first wall 22. The opening 26 is preferably circular also, and for instance, may be about 9 centimeters in diameter. The apparatus per se may be about 10 centimeters in diameter. The peripheral wall 24 has a flange 28 formed at its free end around its periphery and extending at about right angles to the peripheral wall. The flange defines through its surface at predetermined spaced intervals a series of holes 30 of a size suitable to receive therethrough a suturing thread. These holes may, for instance, each be about 1 millimeter in diameter. A nozzle 32 extends from the reservoir, preferably from the peripheral wall 24, and has an opening 34 extending through the nozzle and opening into the interior of the reservoir. The nozzle, which may be about 15 millimeters long, is adapted to receive thereover one end of the catheter 12 as illustrated in the drawings.

A needle-penetrable covering 36 extends across the opening 26 of the reservoir and is suitably secured to the peripheral wall as by being secured to the flange 28 with an appropriate adhesive. The covering is preferably a velour made from a suitable polyester material and must be sufficiently permeable to allow body tissue ingrowth to occur and to seal the surface of the covering as it extends across the opening 26 when the apparatus 10 is surgically implanted in a patient. This sealing by the body tissues prevents leakage of any solutions from the reservoir into the surrounding body tissues.

The reservoir is also provided with an essentially nonyielding support 38 for the needle-penetrable covering 36 and extends across the opening 26 of the reservoir beneath and contiguous with the undersurface of the covering and is suitably fixed to the peripheral wall 24 as by welding. The support 38 is spaced at predetermined intervals across the undersurface of the covering. The support may comprise a series of spaced bars 40 formed in a predetermined pattern, such as in the form of spaced parallel bars as shown in FIG. 2. The spaced bars 40 are preferably also formed of titanium, and may, for example, be about 1 millimeter in diameter. Obviously, the spaced bars could also be formed into a diamond pattern, a pattern of rectangles, or any other pattern to serve the purpose of support for the needle-penetrable covering.

The essentially nonyielding support 38 is critical to the invention because it prevents sagging of the body tissues overlying the opening 26 and needle-penetrable covering 36 of the reservoir when the apparatus is in implanted position, thereby preventing intrusion of the body tissues into the interior of the reservoir, especially when needle injections are made. The needle must penetrate through the body tissues and the needle end must be entirely clear of them before the dialysate solution can be introduced into the reservoir. If the body tissues are allowed to sag or be pushed into the reservoir and against the first wall 22 by the needle, the end of the needle might not extend free and clear of the body tissues and thus the dialysate solution could undesirably go into the body tissues.

In reference to FIGS. 4 and 5, FIG. 4 illustrates diagrammatically a part of the body 42 of a patient with the umbilicus being shown at 44. The skin of the patient is suitably sterilized and a midline incision 46 is made slightly above the umbilicus so that the incision extends through the skin 48, subcutaneous fat 50, peritoneum 52 and opening into the peritoneal cavity 54 of the patient, as shown in FIG. 5.

The incision does not affect the muscle layer 56 or the fascia 57 because there is no muscle layer at that location. The apparatus 10 is then surgically implanted in the patient, preferably at approximately the location shown in FIG. 4, so as to allow the attached catheter 12 to extend at the proper angle into the peritoneal cavity. As illustrated in FIG. 5, the apparatus 10 lies beneath the skin and in an area overlying the fascia 57 and muscle layer 56 and tunneled in a pocket formed partly within the subcutaneous fat. The apparatus is then suitably sutured into position by passing the sutures through the holes 30 (not shown in FIG. 5) in the flange 28 and in the subcutaneous fat. The cuff 14 around the catheter may also be made of a polyester material and is positioned within a tunnel formed in the subcutaneous fat. After healing, tissue ingrowth will serve to hold the cuff firmly in place, but it does not extend into the peritoneal cavity. The catheter 12 extends from the apparatus 10 and into the peritoneal cavity, as previously mentioned.

It takes approximately one week for tissue ingrowth to occur. After this, the patient is then ready for peritoneal dialysis to be performed by use of the now surgically implanted apparatus. The skin of the patient is sterilized at the site of the needle-injection to be made, the needle (not shown) being connected by means of a tube (also not shown) to a supply of dialysate solution, as known in the art. It takes approximately 10 to 15 minutes for the dialysate to be introduced into the peritoneal cavity. The patient may lie down to receive the dialysis. After the dialysate has been introduced, about 1 to 2 liters depending upon the size of the patient, the needle is removed, and then the patient may go about his or her business. Approximately four hours later, he or she returns to receive another needle injection by which the dialysate solution and accumulated toxins and the like are drained from the peritoneal cavity, either by gravity or vacuum technique, and then a fresh dialysate solution is introduced through the needle as it extends into the interior of the reservoir 20. Drainage also takes about 10 to 15 minutes. For instance, a patient may be dialyzed first at about 7:00 a.m.; then about 11:00 a.m.; about 3:00 p.m. and finally about 7:00 p.m. As may be noted, these injections take place usually during the normal waking hours, and none need take place during normal sleeping hours. This schedule is suitable for a patient who has a chronic condition and thus needs peritoneal dialysis all the time, say three to four times during the day.

In order to allow each needle injection site to properly heal before being used again, which may take about 3 to 5 days, I have provided a novel method by which optimum healing may take place.

The method involves providing on the surface of the skin of the patient at a location overlying the opening 26 in the surgically implanted apparatus a diagram 58, such as shown in FIG. 6, corresponding in size and configuration to the opening. The diagram 58 may preferably be sketched on the patient by any suitable means such as by a cotton swab dipped in gentian violet. It does not have to be a precise sketch so long as it overlies the opening of the reservoir. The diagram is preferably divided into approximately equal segments in size and configuration, and a series of marked points 60 are then provided within each segment at predetermined spaced intervals, such as 8 to 10 millimeters apart. Each marked point designates the site for the entry of a needle-injection and the spaced intervals will then correspond to the spacing necessary to avoid a yet unhealed area caused by more recent needle-injections. Each needle-injection, then, will be made at a marked point 60 different from the previous needle-injection; thus following a predetermined path from one marked point to the next marked point within each segment. For instance, if the opening of the reservoir is circular as shown, then the diagram 58 will be circular in configuration as shown in FIG. 6. The series of marked points 60 may then be located at spaced intervals along concentric circular paths relative to the center of the reservoir opening 26, and the circle may be divided into quarter segments, as also illustrated in FIG. 6.

The needle-injections may then be made consecutively at each of the marked points along each of the circular path portions within one of the quarter-segments, starting with the marked points in the radially outermost circular path portion and finishing with the radially innermost circular path portion, and then proceeding to the marked points in the radially outermost circular path portion in the next adjacent quarter segment to commence needle-injections there.

Obviously, the patient may follow other paths so long as he establishes some desirable predetermined path to avoid using the site of a previous needle-injection that has not as yet healed. This method thus allows sufficient healing to take place before the approximate area of the site is used again.

It will thus be recognized by those skilled in the art that the use of my apparatus, as surgically implanted, will greatly minimize the risk of peritonitis since there will be no catheters extending through and from the skin of the patient. Thus the patient may bathe or swim as he or she pleases without worrying about bacteria entering exposed catheters. Needle-injections through the skin readily heal to prevent bacteria from entering, assuming that the needle and skin site of the needle-injection have both been properly sterilized. From a cosmetic standpoint, there are no exposed catheters extending from the patient's body. The diagram can be washed away, if the patient plans to do any public swimming or the like, and the diagram can be readily re-established by the patient locating with his or her fingers through the skin the peripheral wall and opening therein of the apparatus.

It will also be recognized by those skilled in the art that the apparatus of my invention minimizes to a large degree morbidity, hospitalization due to such morbidity, and the inherent expenses therefrom. This apparatus, therefore, will significantly participate in the cost containment, which is a very essential issue in these times in the delivery of health services.

Although the apparatus may take other configurations, a circular one is preferable from the standpoint of comfort to the patient. The first wall 22 may be flat as illustrated, or slightly curved. The peripheral wall 24 may also be slightly curved or at a slight inclination with respect to the first wall 22, with the angle between the first wall and the peripheral wall being about a right angle.

The invention has been described in detail with particular reference to preferred embodiments thereof, but it will be understood that variations and modifications can be effected within the spirit and scope of the invention.

I claim:

1. Surgically implantable apparatus adapted for subcutaneous placement in the body of a patient and by which peritoneal dialysis may be performed, said apparatus comprising:

reservoir means defining a first wall, and a peripheral wall formed at the periphery of the first wall at about right angles thereto and extending a predetermined distance therefrom and defining at its free end of opening opposite the first wall, said reservoir means being formed from a needle-impenetrable material;

needle-penetrable covering means extending across the opening of said reservoir means and suitably secured to said peripheral wall and being sufficiently permeable to allow body tissue ingrowth to occur and to seal the surface of said covering means when the apparatus is implanted in a patient;

an essentially nonyielding support means for said needle-penetrable covering means extending across said opening beneath and contiguous with the undersurface of said covering means and suitably fixed to said peripheral wall and spaced at predetermined intervals across the undersurface of said covering means, said essentially nonyielding support means comprising a series of spaced bars formed in a predetermined pattern; and means defining a nozzle extending from said reservoir means and having an opening extending therethrough and into the interior of said reservoir means, said nozzle being adapted to receive thereover one end of a catheter that will extend into the peritoneal cavity of the patient.

2. A surgically implantable apparatus as defined in claim 1, wherein said peripheral wall has a flange formed at its free end around its periphery and extending outwardly from the peripheral wall at about right angles thereto, said flange defining through its surface at predetermined spaced intervals a series of holes of a size suitable to receive therethrough a suturing thread.

3. A surgically implantable apparatus as defined in claim 1 wherein said reservoir means is formed from titanium.

4. A surgically implantable apparatus as defined in claim 2 wherein said covering means is suitably secured to said flange.

5. A surgically implantable apparatus as defined in claim 1 wherein said nozzle extends from said peripheral wall.

6. A surgically implantable apparatus as defined in claim 1 wherein said first wall of said reservoir means is circular and said peripheral wall extends circumferentially around the periphery of said first wall.

7. A surgically implantable apparatus as defined in claim 1 wherein said series of spaced bars are spaced parallel bars.

8. Method of performing peritoneal dialysis on a patient in whose body the apparatus defined in claim 1 has been suitably surgically implanted in such manner that said opening and said needle-penetrable covering means of the apparatus are spaced below and parallel to the skin of the patient and a catheter has been connected to the nozzle means of the apparatus and extended from the apparatus and into the peritoneal cavity of the patient, the method comprising:

providing on the surface of the skin of the patient at a location overlying the opening in the surgically implanted apparatus a diagram corresponding approximately in size and configuration to said opening, the diagram being divided into approximately equal segments in size and configuration and having a series of marked points within each segment at predetermined spaced intervals, each marked point designating the site for the entry of a needle-injection and the spaced intervals corresponding to the spacing necessary to avoid a yet unhealed area caused by more recent needle-injections; and making each needle-injection at a marked point different from the previous needle-injection and following a predetermined path from one marked point to the next marked point within each said segment.

9. The method according to claim 8 wherein said diagram is in the configuration of a circle and said series of marked points are located at spaced intervals along concentric circular paths relative to the center of said opening, and said circle is divided into quarter segments.

* * * * *